(12) United States Patent
Lubock et al.

(10) Patent No.: US 7,465,268 B2
(45) Date of Patent: Dec. 16, 2008

(54) METHODS FOR ASYMMETRICAL IRRADIATION OF A BODY CAVITY

(75) Inventors: Paul Lubock, Laguna Niguel, CA (US); Michael L. Jones, San Clemente, CA (US); Frank R. Louw, Carlsbad, CA (US)

(73) Assignee: SenoRx, Inc., Aleso Viejo, CA (US)

( * ) Notice: Subject to any disclaimer, the term of this patent is extended or adjusted under 35 U.S.C. 154(b) by 0 days.

(21) Appl. No.: 11/593,789

(22) Filed: Nov. 6, 2006

(65) Prior Publication Data

US 2007/0167667 A1    Jul. 19, 2007

Related U.S. Application Data

(63) Continuation of application No. 11/283,236, filed on Nov. 18, 2005.

(60) Provisional application No. 60/819,919, filed on Jul. 11, 2006.

(51) Int. Cl.
*A61N 5/00* (2006.01)

(52) U.S. Cl. .......................................................... 600/3

(58) Field of Classification Search ................. 600/1–9, 600/30, 407, 424, 427; 601/1, 15, 111, 112, 601/118, 119; 604/19–21, 27–28, 48, 73, 604/93.01, 95.03, 96.01, 101.01–101.05, 604/102.01–102.03, 103.05–103.07, 103.1, 604/104, 158–159, 164.01, 164.08, 171, 604/263–264, 500, 506–511, 514–517; 606/1, 606/32–34, 41; 607/1–2, 100, 101, 122, 607/154–156

See application file for complete search history.

(56) References Cited

U.S. PATENT DOCUMENTS

| 3,872,856 A | 3/1975 | Clayton |
|---|---|---|
| 4,690,677 A | 9/1987 | Erb |
| 5,106,360 A | 4/1992 | Ishiwara et al. |
| 5,621,780 A | 4/1997 | Smith et al. |
| 5,720,717 A | 2/1998 | D'Andrea |
| 5,935,098 A | 8/1999 | Blaisdell et al. |
| 6,036,631 A | 3/2000 | McGrath et al. |

(Continued)

FOREIGN PATENT DOCUMENTS

EP    0 642 766    3/1995

(Continued)

OTHER PUBLICATIONS

Written Opinion of the International Searching Authority for PCT/US2006/043891 mailed Sep. 25, 2007.

(Continued)

*Primary Examiner*—John P Lacyk
(74) *Attorney, Agent, or Firm*—Edward J. Lynch

(57) ABSTRACT

The disclosure describes devices and methods for asymmetrical irradiation at a body cavity or site, such as after removal of tissue, e.g. biopsy or cancer. One device includes a lumen which is off-set or off-settable from a longitudinal axis to increase the intensity of radiation received from a radiation source by a first tissue portion surrounding the body cavity and to reduce or minimize radiation received by a second tissue portion (e.g. healthy tissue) surrounding the body cavity.

5 Claims, 6 Drawing Sheets

U.S. PATENT DOCUMENTS

| | | | |
|---|---|---|---|
| 6,390,967 B1 | 5/2002 | Forman et al. | |
| 6,413,203 B1 | 7/2002 | Sahatjian | |
| 6,416,492 B1 | 7/2002 | Nielson | |
| 6,482,142 B1* | 11/2002 | Winkler et al. | 600/3 |
| 6,540,655 B1 | 4/2003 | Chin et al. | |
| 6,706,014 B2 | 3/2004 | Banik et al. | |
| 6,913,600 B2 | 7/2005 | Valley et al. | |
| 6,923,754 B2 | 8/2005 | Lubock | |
| 7,404,791 B2 | 7/2008 | Lunares et al. | |
| 2001/0016725 A1 | 8/2001 | Valley et al. | |
| 2004/0054366 A1 | 3/2004 | Davison et al. | |
| 2004/0260142 A1 | 12/2004 | Lovoi | |
| 2005/0080313 A1 | 4/2005 | Stewart et al. | |
| 2005/0124843 A1 | 6/2005 | Singh | |
| 2006/0100475 A1 | 5/2006 | White et al. | |
| 2006/0167416 A1* | 7/2006 | Mathis et al. | 604/164.01 |
| 2006/0173235 A1* | 8/2006 | Lim et al. | 600/6 |

FOREIGN PATENT DOCUMENTS

| | | |
|---|---|---|
| EP | 0 719 571 | 7/1996 |
| EP | 0 867 200 | 9/1998 |
| EP | 1 402 922 | 3/2004 |
| EP | 1 618 924 | 1/2006 |
| WO | WO 95/20241 | 7/1995 |
| WO | WO 97/45053 | 12/1997 |
| WO | WO 01/43826 | 6/2001 |
| WO | WO 01/58346 | 8/2001 |
| WO | WO 2004/043531 | 5/2004 |
| WO | WO 2007/027831 | 3/2007 |

OTHER PUBLICATIONS

International Search Report for PCT/US2006/043891 mailed May 11, 2007.

"Variable shield for radiation-therapy source wire and centering catheter", Research disclosure, Mason Publications, Hampshire, GB, vol. 438, No. 48, Oct. 2000, XP007126916.

International Search Report for PCT/US2006/044067 mailed Dec. 18, 2007.

Written Opinion of the International Searching Authority for PCT/US/2006/044067 mailes Dec. 18, 2007.

* cited by examiner

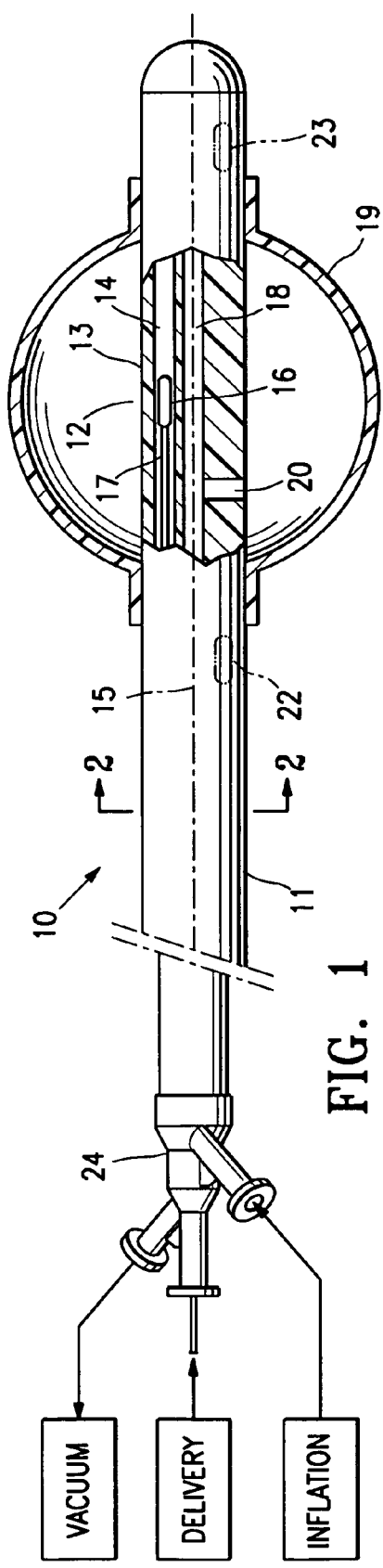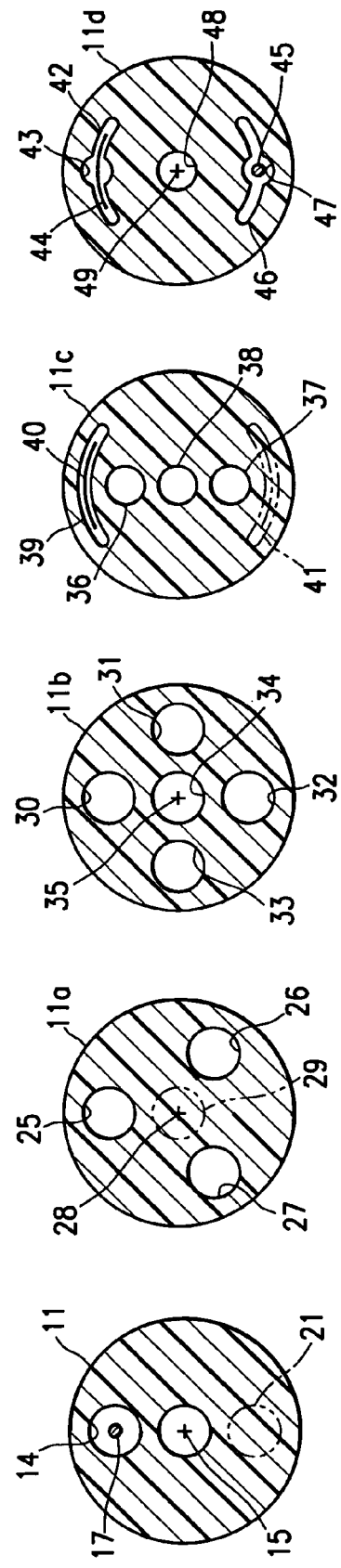

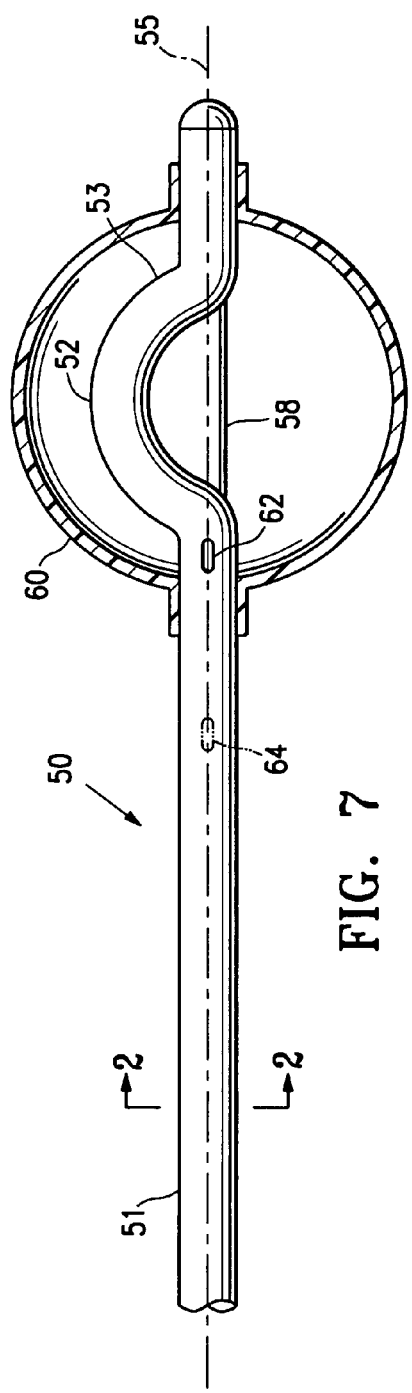
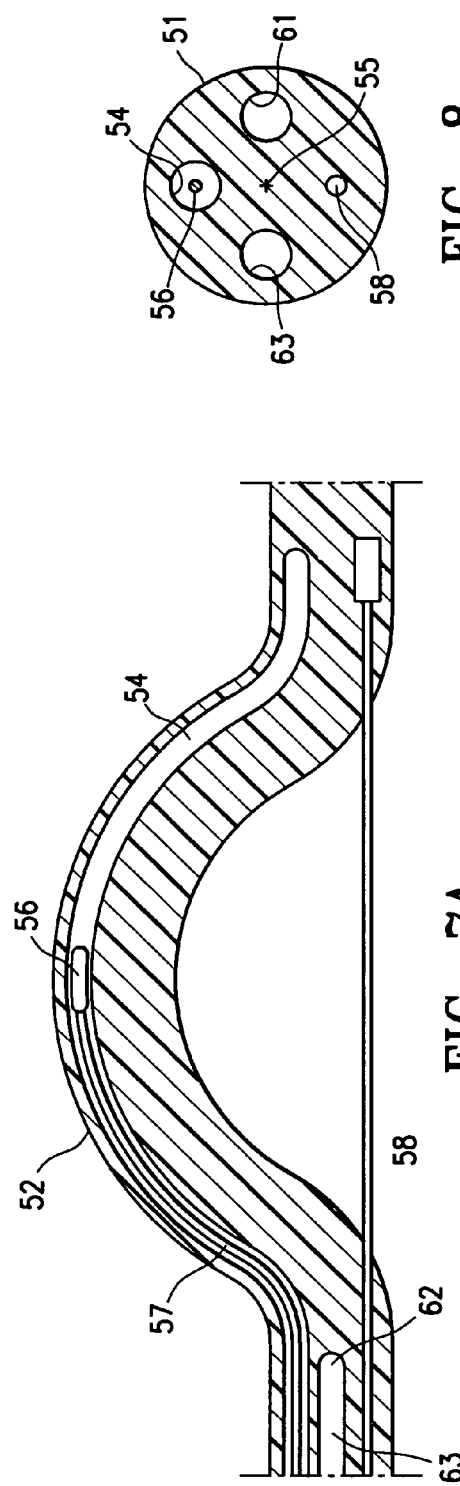

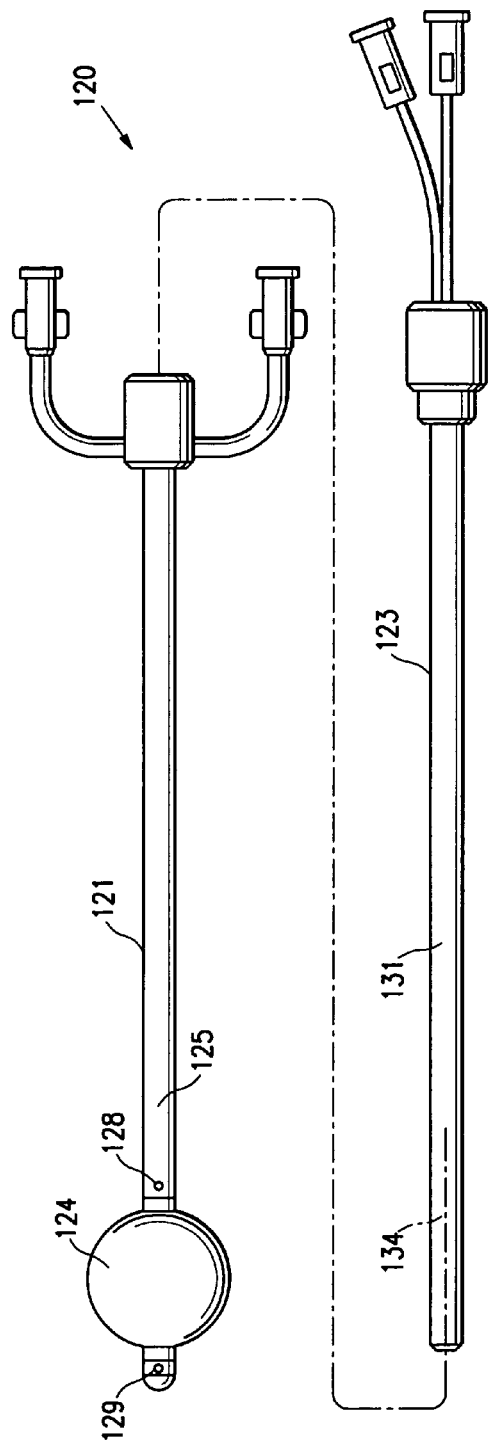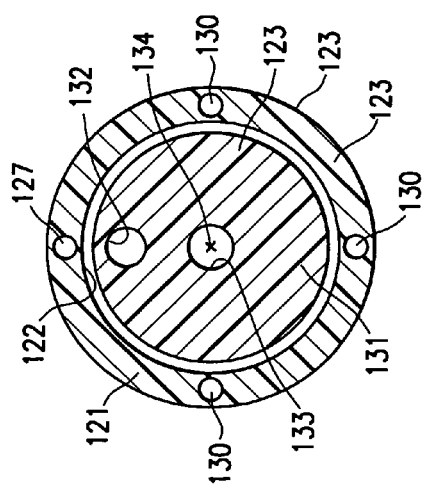
FIG. 13A
FIG. 13B

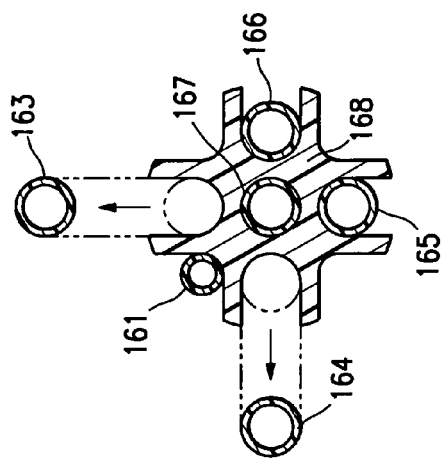
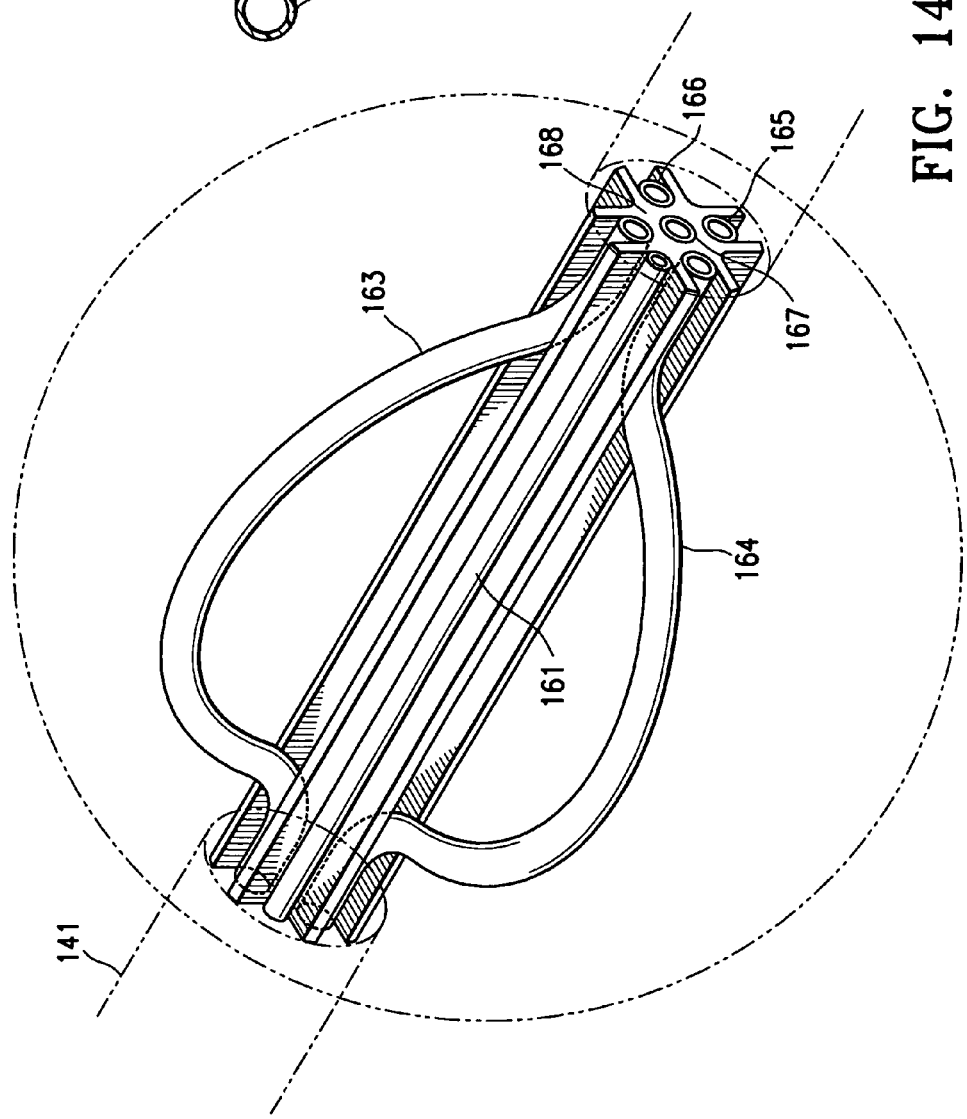

METHODS FOR ASYMMETRICAL IRRADIATION OF A BODY CAVITY

RELATED APPLICATIONS

This application is related to and claims priority from provisional application Ser. No. 60/819,919 filed on Jul. 11, 2006, entitled Radiation Device For A Body Cavity, which is incorporated herein by reference in its entirety. This application also is a continuation of application Ser. No. 11/283,236, filed Nov. 18, 2005, from which priority is also claimed.

FIELD OF THE INVENTION

This invention relates generally to the fields of medical treatment devices and methods. In particular, the invention relates to devices and methods for treating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Iotrex®, Proxima Therapeutics, Inc.). A radiation source such as a miniature or micro-miniature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when only the portion of tissue requiring treatment receives the radiation and where surrounding healthy tissue is unaffected. Tissue cavities typically are not uniform or regular in their sizes and shapes, so that differences in dosages applied to different regions of surrounding tissue, including "hot spots" and regions of relatively low dosage, often result from radiation treatment.

A treatment delivery device for treating tissue adjacent a body cavity has been disclosed in U.S. Pat. No. 6,923,754. This device applies a partial-vacuum or suction to bring tissue towards a radiation source and allows for uniform application of radiation to tissue surrounding a body cavity. An advantage of the present invention is that it allows for the protection of healthy tissue within that body cavity and provides a seal in the passageway leading to the body cavity while treating the desired tissue.

SUMMARY OF THE INVENTION

This invention is generally directed to treating a patient's body cavity or other intracorporeal site (hereinafter collectively referred to as a body cavity) and devices and methods for such treatments. The invention is particularly suitable for treating tissue adjacent to a body cavity formed by the removal of tissue such as in a biopsy or lumpectomy.

More specifically, a device embodying features of the invention has a distal portion with a treatment location which is configured to be asymmetrically deployed within the body cavity so as to be closer to a first portion of tissue surrounding the cavity than a second portion of tissue surrounding the cavity opposite the first tissue portion. The treatment location of the distal portion which includes or is configured to receive a radiation source such as a brachytherapy seed or other irradiating agent for irradiating the first portion of tissue surrounding the body cavity more intensely that the second portion of tissue surrounding the body cavity opposed to the first portion of tissue due to the radiation source being closer to the first tissue portion than to the second tissue portion.

In one embodiment the treatment location having a radiation source is offset or capable of being offset within the body cavity so that tissue of the first portion of the cavity receives more intense radiation treatment than the tissue of the second portion.

This invention is generally directed to treating a patient's body cavity or other intracorporeal site and devices and methods for such treatments. The invention is particularly suitable for treating tissue adjacent to a body cavity such as a cavity formed by the removal of tissue.

More specifically, a device embodying features of the invention has a distal portion with a treatment location which is configured to be asymmetrically deployed within the body cavity and which is configured to receive or which includes a brachytherapy or other irradiating agent for treating tissue surrounding the cavity or other site.

In one embodiment the treatment location having a radiation source is offset or capable of being offset from the central location within the body cavity so that tissue of one portion of the cavity receives more intense radiation treatment than the tissue of an opposing portion.

The invention is generally directed to treating a patient's body cavity by irradiation, and devices and methods for such treatments. The invention is particularly suitable for treating tissue adjacent a patient's body cavity, such as that formed by removal of tissue for a biopsy.

More specifically, a device embodying features of the invention includes a treatment location at a distal portion of the device which is configured to receive or which includes a brachytherapy agent, such as a radiation source and which has a centrally located longitudinal axis. The distal portion of the shaft with the treatment location is deployable within the body cavity so as to provide asymmetrical treatment such as irradiation thereto to tissue surrounding the cavity and is or is capable of being deployed away from the longitudinal axis and closer to one portion of the cavity than an opposed portion.

In one embodiment the distal portion of the device has at least one delivery lumen which is configured to receive a radiation source and which is off-set or capable of being off-set from a central longitudinal axis so that the radiation source is closer to the tissue of the first portion of the body cavity than the tissue of the second portion of the cavity at an opposing side resulting in greater levels of radiation being received by the first tissue portion of the cavity. In this embodiment the device may also have one or more radiation shielding components that provide further control of the radiation emitted from the radiation source, such as described in concurrently filed application Ser. No. 11/593,952, entitled Tissue Irradiation With Shielding. Off-setting the lumen in which the radiation source is deployed places the radiation source closer to a first tissue portion surrounding the body cavity to provide greater levels of radiation thereto and further away from the second tissue portion surrounding the body cavity at other locations to reduce the level of radiation thereto. The radiation received by the tissue surrounding the body cavity is a function of inverse of the distance (R) from the radiation source squared ($1/R^2$), so even small changes in the location of the radiation source within a body cavity can make a significant impact on the amount of radiation received by tissue in the body cavity or site. In this embodiment the shaft having the distal portion with the treatment location may be deformed to deflect the radiation lumen to an off set location with respect to the central longitudinal axis. An alternative is to provide an asymmetrical cavity filling member that holds the distal portion of the shaft with the treatment location at a desired position within the cavity or body site to provide asymmetrical irradiation to the tissue surrounding the cavity or site. This maybe accomplished with a cavity filling member that is asymmetrical, is mounted asymmetrically on the shaft or is configured to be inflated to an asymmetrical shape. The cavity filling member may have separate chambers which are independently inflated to different sizes so as to develop an asymmetrical shape that results in an off-set of the radiation source.

In another embodiment the device has an outer sheath with an inner lumen and an inner cannula or catheter which is rotatably disposed within the inner lumen of the outer sheath. The cannula or catheter has an inner lumen which is configured to receive a radiation source. The inner lumen receiving the radiation source is off set from a central longitudinal axis of the catheter or cannula, so that rotation of the cannula or catheter within the inner lumen of the outer sheath will adjust the position of a radiation source within the body cavity or site to provide the desired asymmetrical irradiation dose within the cavity.

The elongated shaft may also have one or more radiation shielding components designed to reduce or minimize damaging irradiation of healthy tissue surrounding the body cavity while treating nearby areas having diseased tissue with radiation emitted from the radiation source. The radiation shielding components include one or more radiation shields disposed about a delivery shaft containing the radiation source. Suitable radiation shielding components are describe in copending application Ser. No. 11/593,952, filed concurrently herewith, entitled Tissue Irradiation With Shielding.

A device embodying features of the invention preferably has an enlarged or enlargeable cavity filling member at the treatment location which at least in part fills the body cavity. Preferably, the cavity filling member is inflatable member such as a balloon. The elongated shaft has an inner inflation lumen for directing inflation fluid to the interior of the cavity filling member for its inflation.

The device may also include an inner lumen configured to be in fluid communication with a proximal vacuum source and one or more vacuum ports preferably proximal and or distal to the cavity filling member such as described in U.S. Pat. No. 6,923,754 and co-pending application Ser. No. 10/849,410 filed on May 19, 2004, both of which are assigned to the present assignee. Application of a vacuum within the inner lumen aspirates fluid in the cavity through one or more vacuum ports and the vacuum within the body cavity pulls tissue defining the cavity onto the exterior of the cavity filling member deployed within the cavity. The application of a vacuum may also be employed to aspirate fluids from the cavity or site.

A method for treating a body cavity or other intracorporeal site of a patient includes delivering a treatment agent such as a radiation source to a body cavity to treat the desired tissue while minimizing damaging irradiation of healthy tissues. More specifically, a method for treating a body cavity or intracorporeal site includes providing a device having an elongate shaft with a proximal end, a distal end, and a treatment location in a distal portion of the shaft. The method further includes providing a radiation source configured to be deposited in the treatment location and a radiation shielding component partially encircling the treatment location which is configured to control at least in part the emission of radiation emitted from the treatment location. The device is advanced within the patient until the treatment location of the device is deployed within the body cavity or site and the radiation source is positioned within the treatment location. The radiation shielding component is positioned to shield portions of the body cavity from radiation emitted from the radiation source.

A patient's skin is susceptible to damage from radiation delivered by isotopes (e.g. seeds) or x-ray catheters in a lumen of a radiation balloon catheter if the radiation source is to close to the skin. Generally, radiation treatments using a radiation balloon catheter is usually not performed on patients where the body cavity (e.g. from a lumpectomy) is less than 5 mm, sometimes less than 7 mm from the patient's skin. Additionally, over inflation of the balloon can thin and stretch the skin. The application of a vacuum to the body cavity can help by pulling the tissue to the balloon and increased cavity to skin surface distances would result. However, in some instances it would still be too thin to treat. The number of potential patient's which are suitable candidates for treatments with the present device is significantly increased due to reducing the potential for skin tissue damage.

Placing patterns of radiation absorbing materials on the surface or within the wall of the balloon would aid in shielding the skin or in other cases, sensitive organs (e.g., heart, lung, ribs, etc.) from unnecessary radiation. Examples include—Mylar with aluminum, balloon coatings with gold, lead, titanium barium and barium sulfate or silver ions incorporated within the balloon wall.

The surface (inside or outside) of the balloon or within the balloon wall may be provided with indicator marks for location or orientation detection during the procedures. For example, dots or lines to help place balloon in appropriate position under CT, x-ray or fluoroscopy. The indicator marks may be radiopaque. Alternatively, or additionally, ultrasound indicators or MRI and direct visual indicators could be incorporated. The indicator marks may extend along the catheter shaft to help with placement of the catheter device during the treatment procedure and the orientation of the off set lumen and shield.

In other embodiments having features of the invention, the radiation shield may be secured to a control rod or band within the catheter device so that the location of the shield may be adjusted. Alternatively, the radiation shield may be secured within or onto the catheter device.

These and other advantages of the present invention are described in more detail in the following written description and the accompanying exemplary drawings.

BRIEF DESCRIPTION OF THE DRAWINGS

FIG. 1 is a schematic view, partially in section, of a brachytherapy device embodying features of the invention including a cavity filling member.

FIG. 2 is a transverse cross sectional view of the device shown in FIG. 1 taken along lines 2-2 which illustrates the device with two inner lumens.

FIG. 3 is a transverse cross sectional view of an alternative device similar to the device shown in FIG. 1 having three lumens.

FIG. 4 is a transverse cross sectional view of an alternative device similar to the device shown in FIG. 1 having 5 lumens.

FIG. 5 is a transverse cross-sectional view of an alternative device having three lumens having circular transverse cross-sections and a pair of opposed arcuate inner lumens for radiation shielding component.

FIG. 6 is a transverse cross-sectional view of a device similar to that shown in FIG. 1 which has a plurality of arcuate lumens with enlarged central portions which allow for the deployment of a radiation shield or a radiation source within the lumens.

FIG. 7 is an elevational view, partially in section, of a distal portion of an alternative design for a brachytherapy device wherein the shaft within the cavity filing member is deformed to place the radiation source closer to one side of the cavity filling member than an opposed site.

FIG. 7A is an enlarged longitudinal cross-section of the deformed shaft within the cavity filling member.

FIG. 8 is a transverse cross-sectional view of the device shown in FIG. 7 taken along the lines 8-8.

FIGS. 13A-B illustrate another embodiment having features of the invention which has an outer catheter with a cavity filling member and an inner catheter with an inner lumen which is off set or off settable from a longitudinal axis.

FIG. 14C is a perspective view of a compartmented support member and tubular members which extend through an inflatable member.

FIG. 14D is a transverse cross-sectional view of the device shown in FIG. 14A taken along the lines 14D-14D.

DETAILED DESCRIPTION OF THE INVENTION

Figure 10:
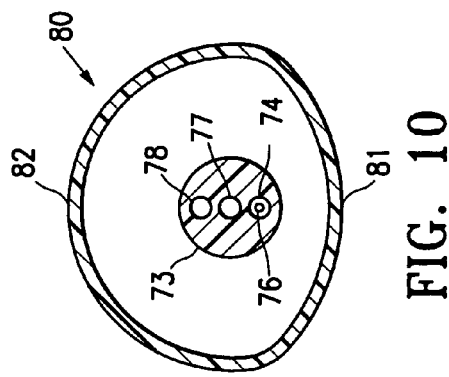
FIG. 10 is a transverse cross-sectional view of the brachytherapy device shown in FIG. 9 taken along the lines 10-10.

The present invention is directed to devices and methods for treatment of a patient's body cavity, particularly to deliver asymmetrical radiation into a biopsy cavity or into a cavity left after removal of tissue from the patient's body. Other body sites may also be treated.

FIGS. 1 and 2 illustrate a brachytherapy device 10 embodying features of the invention which has an elongated shaft 11 with a treatment location 12 in a distal portion 13 of the elongated shaft 11. The elongated shaft 11 has a first lumen 14 which is off set from central longitudinal axis 15 and which is configured to receive a radiation source 16. The radiation source 16 is disposed at the distal end of pusher rod 17 to facilitate deployment within the treatment location 12. The elongate shaft 11 also has a second lumen 18 for delivery of inflation fluid to the interior of the cavity filling member 19 through inflation port 20. The elongated shaft 11 may also have a third lumen 21 shown in phantom to provide a vacuum to a desired location such as vacuum ports 22 and 23 also shown in phantom which are proximal and/or distal to the cavity filling member 19 as described in U.S. Pat. No. 6,923, 641 (assigned to the present assignee). The third lumen may also be utilized as an off-set lumen to receive a radiation source in the event the first lumen 14 is not in a desired location when the distal end of the device is placed in the patient and the physician does not wish to rotate the device 10. The proximal end of the elongated shaft 11 has a multi-arm adapter 24 for delivery of a vacuum, inflation fluid and radiation source as shown. The device 10 may also have one or more radiation shielding components (not shown) to further reduce radiation to tissue which is not to be treated. Suitable radiation shielding components are described in copending application Ser. No. 11/593,952, filed concurrently herewith entitled Tissue Irradiation With Shielding which has been assigned to the present assignee.

A body cavity within a patient may be treated with the device 10 by inserting the distal shaft portion 13 into the desired body cavity with the off-set first lumen 14 configured to receive the radiation source 16 being closer to a first tissue portion surrounding the cavity to be treated and farther away from a second tissue portion surrounding the cavity which needs to be protected. A radiation source 16 is advanced within the first lumen 14 until the radiation source is properly positioned within the treatment location 12 (or prepositioned therein). Inflation fluid is delivered to the interior of the cavity filling member 19 so as to at least partially fill the body cavity. A vacuum may be generated about the cavity filling member 19 through vacuum ports 22 and 23 to conform the tissue surrounding the cavity to the exterior of the cavity filling member. The radiation source 16 is maintained at the treatment location 12 for a prescribe period of time, usually less than 30 minutes and typically a few (5-10) minutes. At the end of the treatment time the radiation source may be removed from device 10 or the entire device may be withdrawn from the patient. Preferably, the device is left in place so that further radiation treatments may be performed.

FIG. 3 illustrates an elongated shaft 11a of an alternative brachytherapy device which has three off-set lumens 25, 26 and 27 that are equally disposed about the longitudinal axis 28. The first off-set lumen 25 may be used as the radiation delivery lumen such as described above for first lumen 14. The second and third off-set lumens 26 and 27 may be utilized for delivery of inflation fluid to the interior of a cavity filling member (not shown) or for delivery of a vacuum to vacuum ports (not shown) proximal or distal to the cavity filling member as described above. Additionally, a centrally located fourth lumen 29 (shown in phantom) may be provided as an alternative lumen for radiation delivery in the event an off-set location is not needed. The fourth lumen may also be employed as an inflation or vacuum lumen as described above, leaving one of the off-set lumens 26 and 27 to deliver a radiation source in the event the first off-set lumen is not in a desirable location when the device is deployed within the patient's body cavity.

FIG. 4 illustrates an elongated shaft 11b of another alternative design of device 10 which has four off set lumens 30-33, one central lumen 34 which is axially aligned with longitudinal axis 35. The off set lumens 30-33 and central lumen 34 may be utilized as in the prior embodiments. This embodiment provides additional alternative lumens for delivery of a radiation source (not shown) as described above.

FIG. 5 illustrates yet another elongated shaft 11c of an alternative design which has two off set lumens 36 and 37 and a central lumen 38 which have circular transverse cross-sections as shown. The off set and central lumens 36, 37 and 38 may be utilized as described above. Additionally, at least one arcuate lumen 39 may be provided to facilitate placement of a radiation shield 40 as described in concurrently filed application Ser. No. 11/593,952 entitled Tissue Irradiation With Shielding. A second arcuate lumen 41 at an opposed position within the shaft 11c (shown in phantom) for delivery of a radiation shield in the event the device is not placed in a desired orientation and the physician does not want to rotate the device.

FIG. 6 depicts another elongated shaft 11d for an alternative brachytherapy device 10 which has a first arcuate lumen 42 with an enlarged central portion 43. This first arcuate lumen 42 is design to slidably receive a radiation shielding member 44 and the enlarged central portion 43 is designed to slidably receive a radiation source 45 such as shown in second arcuate lumen 46 with enlarged central portion 47. A central lumen 48 is axially disposed about the longitudinal axis 49 and may be utilized for delivery of inflation fluid or a vacuum to the distal portion of the device. This design allows for the flexibility of placing either a radiation source or a radiation shielding member on either side of the device. The central lumen 48 may alternatively be positioned off-set within the shaft 11d. Other off-set lumens may be provided as described above with respect to the other embodiments.

FIGS. 7, 7A and 8 depict an alternative brachytherapy device 50 which has an elongated shaft 51 with a treatment location 52 in a distal portion 53 thereof. The shaft 51 is deformable within the treatment location 52. The elongated shaft 51 has a first lumen 54 which is configured to receive a radiation source 55 to position a radiation source off set from the longitudinal axis 56. The radiation source 55 has a standard pusher rod 57 to facilitate placement of the radiation source at the treatment location 52 within the first lumen 54. The distal shaft portion 53 is deformed, i.e. radially deflected, by pull-wire 58 so that the treatment location 52 is off-set or further off set from the longitudinal axis 56. The distal end of the pull-wire 58 has an enlarged hub which secures the distal end of the pull-wire within the shaft. The deformation of the distal shaft portion 53 places the radiation source 55 closer to one side of the cavity filling member 60 thereby reducing the radiation to tissue of the opposing side of the cavity. While only one pull-wire 58 is illustrated, multiple pull-wires may be employed about the longitudinal axis 56 to facilitate deformation of the distal shaft portion 53 in multiple directions. Other mechanical structures, may be provided to radially deflect the distal shaft portion 53 away from longitudinal axis 56. Off-set lumen 61 leads to inflation port 62 for directing inflation fluid to the interior of the cavity filling member 60. Off-set lumen 63 leads to vacuum port 64 (shown in phantom) proximal to the cavity filling member 60 to generate a vacuum within the body cavity to aspirate fluids and/or to conform surrounding tissue of the body cavity to the exterior of the cavity filling member 60.

Figure 9:
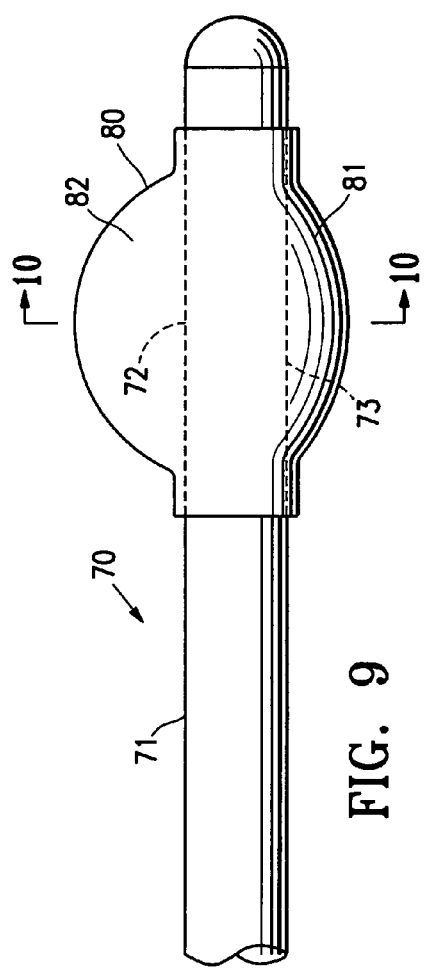
FIG. 9 is an elevational view of a distal portion of an alternative design for a brachytherapy device wherein the cavity filling member is asymmetric, or inflated to an asymmetric configuration to place the radiation source closer to one side of the body cavity or site.

FIGS. 9 and 10 illustrate another brachytherapy device 70 embodying features of the invention. The device 70 has an elongated shaft 71, a treatment location 72 in distal shaft portion 73, a first lumen 74 configured to receive radiation source 76, a second lumen 77 and a third lumen 78 and an asymmetrical cavity filling member 80. The first lumen 74 is closest to the smaller side 81 of the cavity filling member 80 so that radiation through the smaller side 81 of the cavity filling member 80 to adjacent tissue is greater than the radiation through the larger side 82 to adjacent tissue. The larger side 82 of the cavity filling member 80 is placed next to tissue in which the radiation dose is to be minimized, whereas the smaller side 81 is positioned adjacent to tissue which is to receive a higher dose of radiation. The second and third lumens 77 and 78 may be utilized for vacuum and inflation fluid as discussed above with respect to other embodiments.

Figure 11:
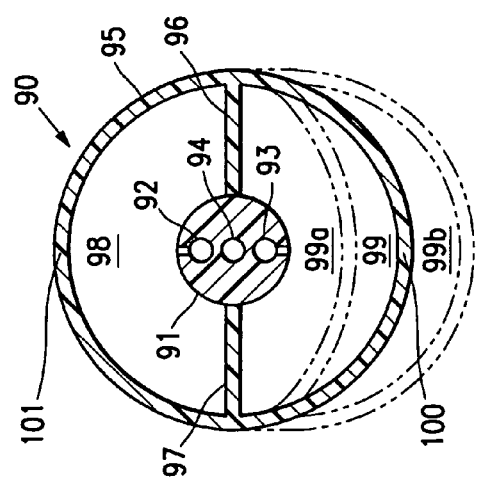
FIG. 11 is a transverse cross-sectional view similar to that shown in FIG. 10 in which the interior of the cavity filling member is separated into two chambers by a membrane so that each chamber may be inflated, e.g. to different sizes.

FIG. 11 shows an alternative brachytherapy device 90 which has an elongated shaft 91 with three inner lumens. Off set lumens 92 and 93 and centrally disposed lumen 94. The first off set lumen 92 is for receiving a radiation source as previously described. The second off set lumen 93 may be for vacuum, inflation fluid or as an alternative lumen for a radiation source. The central lumen 94 may be employed for vacuum, inflation fluid or alternatively a radiation source. The device 90 has a cavity filling member 95 which has inner membranes 96 and 97 which separate the interior of the cavity filling member into separate chambers 98 and 99. Each chamber has separate sources (lumens) for inflation fluid so that one side 100 of the cavity filling member 95 may be inflated to one or more different sizes than an adjacent side 101. As shown in phantom, the side 100 may be inflated to a smaller size 100a or a larger size 100b. Adjusting the sizes controls the location of the radiation source within a lumen. With a smaller size 100a, the tissue to be treated adjacent to side 100 receives a higher radiation dose than tissue adjacent to side 101 which should be protected and given a smaller radiation dose. Alternatively, when chamber 98 is inflated so that side 100 is of a larger size, the tissue adjacent to side 100 will receive more radiation.

Figure 12:
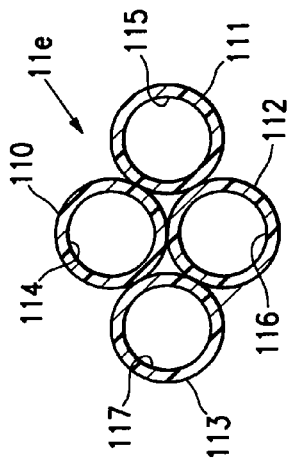
FIG. 12 illustrates a shaft formed of a plurality of elongated elements with at least one of the elongated elements having an inner lumen configured to receive a radiation source.

FIG. 12 depicts an elongate shaft 11e of an alternative device which comprises a plurality of elongated tubular elements 110, 111, 112 and 113. At least one of the elongated elements 110 has a first inner lumen 114 configured for receiving a radiation source such as described above for the other embodiments. The other elongated elements may also have inner lumens 115-117 for delivery of inflation fluid to a cavity filling member (not shown) on a distal portion of the shaft, for delivery of a vacuum to a vacuum port proximal or distal to the cavity filling member or an additional lumen for receiving a radiation source. The plurality of elements 110-113 may be bundled together by one or more outer straps or bands or by an outer sheath or by a suitable adhesive. The plurality of elongated elements of the shaft may be twisted or braided together. Tubular element 110 (as well as 111-113) may be radially deflected as depicted in FIG. 7 to position the first inner lumen closer to the first tissue portion surrounding the body cavity than the second tissue portion.

FIGS. 13A-B illustrate a brachytherapy device 120 which has an outer catheter 121 with an inner lumen 122 and an inner catheter 123 which is configured to be rotatably disposed within the inner lumen 122. The outer catheter 121 has an inflatable cavity filling member 124 on a distal portion 125 of shaft 126. The wall of shaft 126 has at least one lumen 127 for directing inflation fluid to the interior of the cavity filling member 124. The outer catheter 121 also has vacuum ports 128 and 129 proximal and distal to the cavity filling member 124. The wall 130 of shaft 126 has at least one lumen 131 which is in fluid communication with a vacuum port and preferably two lumens. The inner catheter 123 has an elongated shaft 132 with an off-set lumen 133 and may also have a central lumen 134 configured for receiving a radiation source to provide an asymmetrical radiation dose about longitudinal axis 135.

FIGS. 14A-14D illustrate an alternative device 140 which has an elongated shaft 141, a cavity filling balloon 142 on the distal portion of the shaft and an adapter 143 on the proximal end of shaft 141. A plurality of tubes 144-148 extend into the adapter 143 and are in fluid communication with lumens 150-154 respectively within the shaft 141 which are configured to receive radiation sources (not shown) such as those previously described. The device 140 also has an inflation tube 149 which is in fluid communication with lumen 155 that extends to and is in fluid communication with the interior of the balloon 142 to facilitate delivery of inflation fluid thereto. The adapter 143 has a vacuum arm 156 that is in fluid communication with lumens 157 and 158. Lumen 158 is in fluid communication with proximal vacuum port 160 and lumen 157 is in fluid communication with tubular member 161 which in turn is in fluid communication with distal vacuum port 162. Radiation delivery tubes 163-167 are in fluid communication with lumens 150-154. Radiation tube 163 and 164 are radially extended within the interior of balloon 142 in order to be closer to a first tissue portion surrounding a body cavity as previously described. While tubes 163 and 164 are shown as being radially extended within the balloon 142, one radiation delivery tube or more than two radiation delivery tubes may radially extend within the balloon 142 depending upon the need for a particular treatment.

A compartmented support element 168 extends between the proximal and distal ends of the balloon 142. The support element 168 shown has nine compartments 170-174 which are designed to receive tubular radiation delivery members 163-167 respectively. The device 140 may be assembled with the radial extension of radiation delivery tubes 144 and 145 fixed as shown or they may be slidable within the catheter shaft 141 so that the radial extension of these delivery tube be effected during the procedure. The radial extension of the radiation delivery tubes will not usually extend to contact the interior surface of the inflated balloon 142.

The radiation delivery tubes 144-148, which extend into the adapter 143, may extend through the lumens in shaft 141 and may form tubes 163-167 which are received by the support member 163.

All of the radiation delivery tubes which extend through the interior of the balloon 142 would not necessarily be used in a procedure and in fact would probable not be used. However, they would be available for use by the physician if needed, e.g. when the catheter is not in a desired position and rotation of the catheter is not appropriate or desirable. The shaft 141 is shown as a solid shaft having a plurality of passageways. However, the shaft 141 may be made more flexible by utilizing a plurality of tubes which are bundled together form the shaft as shown in FIG. 12.

The radiation source 16 for the brachytherapy device 10 can include a solid or liquid radiation source. Suitable liquid radiation sources include, for example, a liquid containing a radioactive iodine isotope (e.g., $I^{125}$ or $I^{131}$), a slurry of a solid isotope, for example, $^{198}Au$ or $^{169}Yb$, or a gel containing a radioactive isotope. Liquid radiation sources are commercially available (e.g., Iotrex®, Proxima Therapeutics, Inc., Alpharetta, Ga.). The radiation source 16 preferably includes brachytherapy seeds or other solid radiation sources used in radiation therapy, for example, a radioactive microsphere available from 3M Company of St. Paul, Minn. Microminiature x-ray source may also be utilized. The radiation source 16 may be either preloaded into the device 10 at the time of manufacture or may be loaded into the device 10 before or after placement into a body cavity or other site of a patient. Solid radionuclides suitable for use with a device 10 embodying features of the present invention are currently generally available as brachytherapy radiation sources (e.g., I-Plant. TM. Med-Tec, Orange City, Iowa.). Radiation may also be delivered by a device such as the x-ray tube of U.S. Pat. No. 6,319,188. The x-ray tubes are small, flexible and are believed to be capable of being maneuverable enough to reach the desired location within a patient's body.

The brachytherapy device 10 having features of the invention can be provided with a lubricious coating, such as a hydrophilic material. The lubricious coating preferably is applied to the elongate shaft 12 or to the cavity filling member, if one is present, or both to reduce sticking and friction during insertion of a device 10. Hydrophilic coatings such as those provided by AST, Surmodics, TUA Systems, Hydromer, or STS Biopolymers are suitable.

A device 10 having features of the invention may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating preferably is comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating is provided on the elongated shaft of the delivery device 10 at the point where the device 10 enters the skin.

While particular forms of the invention have been illustrated and described herein, it will be apparent that various modifications and improvements can be made to the invention. Some details of the brachytherapy devices have not been disclosed To the extent not otherwise disclosed herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents and all patent applications referred to above in this application as filed are hereby incorporated by reference in their entirety.

What is claimed is:

1. A method for treating tissue surrounding a body cavity of a patient, comprising:
   a) providing a device having an elongated shaft, a distal shaft portion, a treatment location at the distal shaft portion, an expandable cavity filling member disposed about the distal shaft portion with an expanded configuration that at least partially fills the body cavity and at least one tubular member within the treatment location having a distal end coupled to the distal shaft portion, an extended configuration with an arcuate portion curving away from the distal shaft portion and spaced inwardly from the expandable cavity filling member in the extended configuration and a lumen extending within the tubular member having or configured to receive a radiation source;
   b) inserting the device into the patient and advancing the device therein until the treatment location is deployed within the body cavity;
   c) expanding the cavity filling member within the body cavity;
   d) positioning at least one tubular member within the body cavity so that the arcuate portion of the tubular member is closer to a first portion of tissue surrounding the body cavity than a second portion of tissue surrounding the body cavity; and
   e) providing a radiation source within the lumen of at least one tubular member closer to the first portion of tissue surrounding the body cavity to asymmetrically irradiate so that the first portion of tissue surrounding the body cavity receives a greater amount of radiation than the second portion of tissue surrounding the body cavity.

2. The method of claim 1 wherein at least one of the tubular members is deflected to the extended configuration with an arcuate shape in order to position the radiation source within the inner lumen so that the radiation source within the lumen is closer to the first portion of tissue than the second portion of tissue.

3. The method of claim 1 wherein the distal portion of the shaft is deflected by pulling a pull wire connected to the shaft distal to the treatment location.

4. The method of claim 1 wherein the at least one tubular member is positioned within the body cavity by rotating the distal portion to place the radiation source within the lumen of the tubular member closer to the first tissue portion.

5. The method of claim 1 including positioning a radiation shielding component between the radiation source and the second tissue portion to shield the second tissue portion from radiation emitted from the radiation source.

* * * * *

UNITED STATES PATENT AND TRADEMARK OFFICE
CERTIFICATE OF CORRECTION

PATENT NO. : 7,465,268 B2  
APPLICATION NO. : 11/593789  
DATED : December 16, 2008  
INVENTOR(S) : Paul Lubock et al.

Page 1 of 2

It is certified that error appears in the above-identified patent and that said Letters Patent is hereby corrected as shown below:

In the drawings, sheet 1, Fig. 2, the reference numeral --18-- should be applied to the central lumen.

In the drawings, sheet 2, Fig. 7, the cross section "2-2" should be --8-8--; reference numeral "55" should be --56--.

In the drawings, sheet 2, Fig. 7A, reference numeral "56" should be --55--; reference numeral "63" should be --61--.

In the drawings, sheet 2, Fig. 8, reference numeral "56" should be --57--; reference numeral "55" should be --56--.

In the drawings, sheet 3, Fig. 11, reference numeral "99a" should be --100a--; reference numeral "99b" should be --100b--.

In the drawings, sheet 4, Fig. 13A, reference numeral "134" should be --135--; reference numeral "131" should be --132--.

In the drawings, sheet 4, Fig. 13B, beginning at and proceeding clockwise from reference numeral 132: reference numeral "132" should be --133--; reference numeral "134" should be --135--; reference numeral "130" should be --131--; reference numeral "123" second occurrence should be --121--; reference numeral "123" third occurrence should be --126--; reference numeral "130" second occurrence should be --131--; reference numeral "131" should be --132--; reference numeral "133" should be --134--; reference numeral "130" third occurrence should be --131--; reference numeral "121" should be deleted.

Figures 14A, 14B:
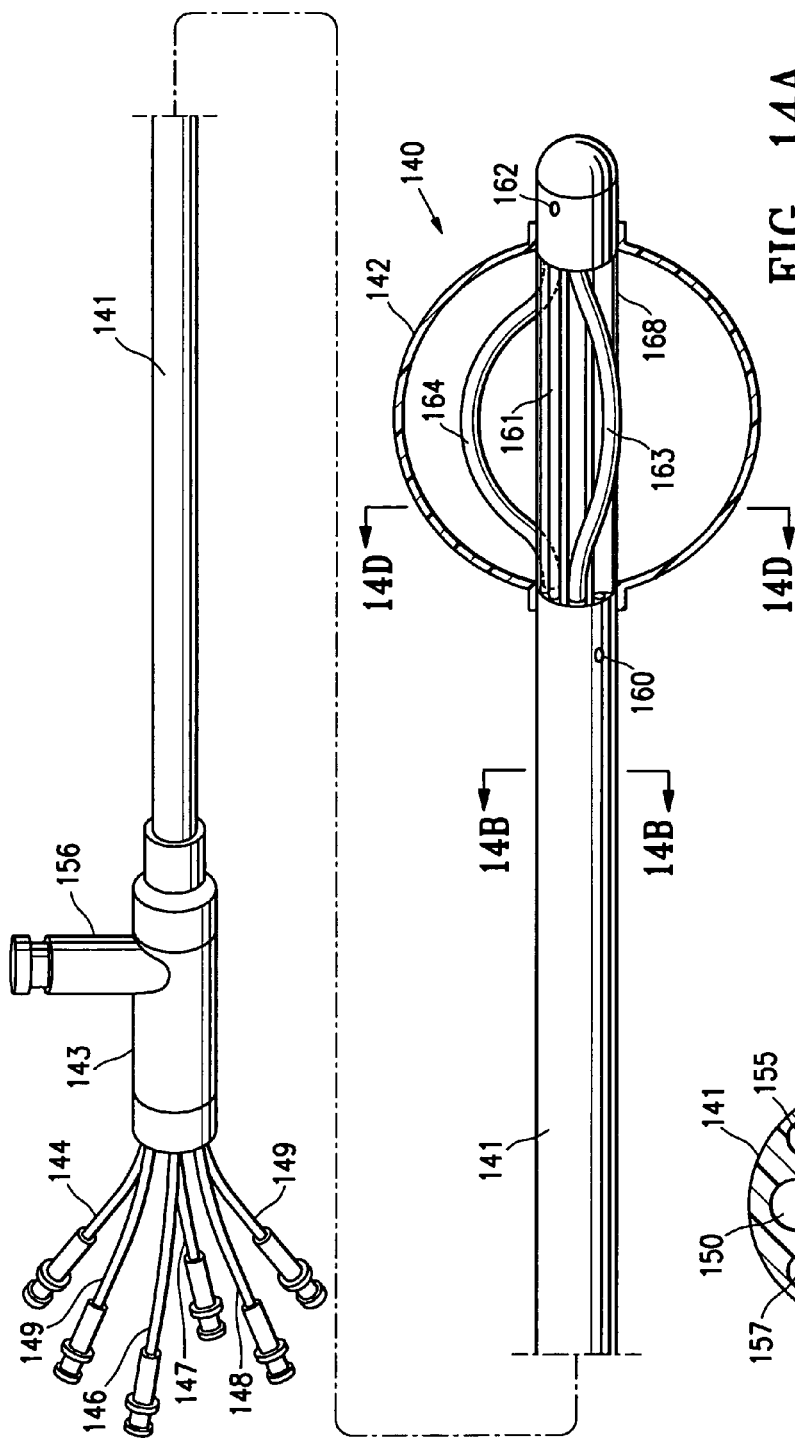
FIG. 14A is a perspective view, partially in section, of an alternative device which has a plurality of radially extending tubular members for delivery of radiation sources.
FIG. 14B is a transverse cross-sectional view of the device shown in FIG. 14A taken along the lines 14B-14B.

In the drawings, sheet 5, Fig. 14A, reference numeral "149" (between tubes 144 and 146) should be --145--.

In the drawings, sheet 5, Fig. 14B, reference numeral "156" should be --151--.

Signed and Sealed this  
First Day of May, 2012

David J. Kappos  
*Director of the United States Patent and Trademark Office*

At column 4, line 22: delete the text "describe" and insert therefor --described--.

At column 9, line 38: delete "130".